US010980966B2

(12) United States Patent
DiMatteo et al.

(10) Patent No.: US 10,980,966 B2
(45) Date of Patent: Apr. 20, 2021

(54) LIQUID CHAMBER DECOUPLING SYSTEM AND METHOD

(71) Applicant: KONINKLIJKE PHILIPS N.V., Eindhoven (NL)

(72) Inventors: Mark William DiMatteo, Irwin, PA (US); Mark Wayne Barclay, Saxonburg, PA (US); Michael Eugene Mort, Somerset, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 506 days.

(21) Appl. No.: 15/536,406

(22) PCT Filed: Dec. 8, 2015

(86) PCT No.: PCT/IB2015/059428
§ 371 (c)(1),
(2) Date: Jun. 15, 2017

(87) PCT Pub. No.: WO2016/097928
PCT Pub. Date: Jun. 23, 2016

(65) Prior Publication Data
US 2017/0361053 A1 Dec. 21, 2017

Related U.S. Application Data

(60) Provisional application No. 62/093,428, filed on Dec. 18, 2014.

(51) Int. Cl.
*A61M 16/10* (2006.01)
*A61M 16/14* (2006.01)
(Continued)

(52) U.S. Cl.
CPC ...... *A61M 16/1045* (2013.01); *A61M 16/024* (2017.08); *A61M 16/109* (2014.02);
(Continued)

(58) Field of Classification Search
CPC .......... A61M 16/1045; A61M 16/1075; A61M 16/108; A61M 16/1085; A61M 16/109;
(Continued)

(56) References Cited

U.S. PATENT DOCUMENTS 4,028,444 A * 6/1977 Brown ................... A61M 16/16
261/122.1
5,037,583 A * 8/1991 Hand ...................... F24F 6/043
222/23

(Continued)

FOREIGN PATENT DOCUMENTS

WO 2011087113 A1 7/2011
WO WO-2011087113 A1 * 7/2011 ............ A61M 16/16

OTHER PUBLICATIONS

English Machine Translation of WO2011087113, Espacenet, All Pages (Year: 2011).*

*Primary Examiner* — Jan Christopher L Merene
*Assistant Examiner* — Brian T Khong

(57) ABSTRACT

A system is configured to prevent damage from liquid spills in a humidified pressure support therapy device. The system includes a decoupler configured to decouple a humidification chamber in a humidifier from a pressure generator of the pressure support therapy device in response to a cover of the humidifier being opened. This eliminates and/or reduces the possibility of liquid in an overfilled humidification chamber unintentionally and/or otherwise entering the pressure generator and damaging sensitive mechanical and/or electrical components. In some embodiments, the system includes one or more of a pressure generator, a humidifier, a subject interface, a sensor, the decoupler, a processor, electronic storage, a user interface, and/or other components.

11 Claims, 8 Drawing Sheets

(51) Int. Cl.
*A61M 16/16* (2006.01)
*A61M 16/00* (2006.01)

(52) U.S. Cl.
CPC ............ *A61M 16/14* (2013.01); *A61M 16/16* (2013.01); *A61M 2016/0039* (2013.01); *A61M 2205/123* (2013.01); *A61M 2205/3365* (2013.01); *A61M 2205/3368* (2013.01); *A61M 2205/3569* (2013.01); *A61M 2205/3592* (2013.01); *A61M 2205/3653* (2013.01)

(58) Field of Classification Search
CPC .. A61M 16/1095; A61M 16/14; A61M 16/16; A61M 16/162; A61M 16/164; A61M 16/0003; A61M 16/0051; A61M 16/0057; A61M 16/006; A61M 2016/0039; A61M 2016/0042; A61M 2205/123; A61M 2205/15; A61M 2205/14; A61M 2205/18; A61M 2205/3569; A61M 2205/3396
USPC .............................................. 261/72.1, 119.1
See application file for complete search history.

(56) References Cited

U.S. PATENT DOCUMENTS

| | | | |
|---|---|---|---|
| 5,445,143 A * | 8/1995 | Sims | A61M 16/167 128/203.26 |
| 5,682,932 A * | 11/1997 | Ediger | F24F 6/00 141/284 |
| 6,024,694 A | 2/2000 | Goldberg et al. | |
| 6,256,454 B1 * | 7/2001 | Dykes | A61G 11/00 392/403 |
| 6,669,626 B1 * | 12/2003 | McDonough | A61G 11/00 600/22 |
| 7,327,949 B1 * | 2/2008 | Cheng | A61M 16/1075 128/203.12 |
| 8,192,001 B2 * | 6/2012 | Umeda | B41J 2/17509 347/2 |
| 9,302,068 B2 | 4/2016 | Shelly | |
| 2007/0132117 A1 * | 6/2007 | Pujol | A61M 16/16 261/119.1 |
| 2007/0169776 A1 * | 7/2007 | Kepler | A61M 16/109 128/200.23 |
| 2008/0066751 A1 * | 3/2008 | Polacsek | A61M 16/16 128/204.17 |
| 2008/0072900 A1 * | 3/2008 | Kenyon | A61M 16/16 128/204.18 |
| 2009/0050151 A1 | 2/2009 | Fuhrman et al. | |
| 2010/0065051 A1 * | 3/2010 | Potharaju | A61M 16/0066 128/203.26 |
| 2010/0242963 A1 * | 9/2010 | Brieger | A61M 16/167 128/203.26 |
| 2011/0155132 A1 * | 6/2011 | Virr | A61M 16/0816 128/203.26 |
| 2011/0233085 A1 * | 9/2011 | Goldie | E05G 1/04 206/317 |
| 2012/0146251 A1 * | 6/2012 | Heine | A61M 16/16 261/128 |
| 2013/0008440 A1 * | 1/2013 | Maurer | A61M 16/109 128/203.12 |
| 2013/0199524 A1 | 8/2013 | Hardin et al. | |
| 2013/0229098 A1 * | 9/2013 | Pletcher | E05C 9/06 312/237 |
| 2014/0158129 A1 * | 6/2014 | Pratt, Jr. | A61M 16/0078 128/203.26 |
| 2014/0216459 A1 * | 8/2014 | Vos | A61M 16/1095 128/204.17 |
| 2014/0332003 A1 * | 11/2014 | Crumblin | A61M 16/0051 128/203.27 |
| 2015/0027204 A1 * | 1/2015 | Stoks | A61M 16/1095 73/31.05 |
| 2015/0048530 A1 * | 2/2015 | Cheung | A61M 16/16 261/129 |
| 2015/0165146 A1 * | 6/2015 | Bowman | A61M 16/0069 128/203.14 |

* cited by examiner

LIQUID CHAMBER DECOUPLING SYSTEM AND METHOD

CROSS-REFERENCE TO PRIOR APPLICATIONS

This application is the U.S. National Phase application under 35 U.S.C. § 371 of International Application Serial No. PCT/IB2015/059428, filed on 8 Dec. 2015, which claims the benefit of U.S. Application Ser. No. 62/093,428, filed on 18 Dec. 2014. These applications are hereby incorporated by reference herein.

BACKGROUND

1. Field

The present disclosure pertains to a system and method for decoupling a humidification chamber from a pressure generator in a humidified pressure support therapy system.

2. Description of the Related Art

Typically, humidifiers are often used with positive airway pressure (e.g., CPAP) devices to alleviate discomfort associated with forced air drying out the oral-nasal cavities during use. The most conventional type of humidifier in homecare ventilation is a passover-type humidifier in which the air from the positive airway pressure device flows into a water chamber and over an area of water. This carries moisture via a patient circuit to a patient. Humidifiers are often directly connected to a pressure generator of the positive airway pressure device.

SUMMARY

Accordingly, one or more aspects of the present disclosure relate to a system configured to prevent damage from liquid spills in a humidified pressure support therapy device. The system comprises a pressure generator, a humidifier, and a decoupler. The pressure generator is configured to generate a pressurized flow of breathable gas for delivery to an airway of a subject. The pressure generator comprises an outlet port configured to conduct the pressurized flow of breathable gas from the pressure generator. The humidifier is configured to humidify the pressurized flow of breathable gas. The humidifier comprises a humidification chamber configured to hold a liquid that humidifies the pressurized flow of breathable gas. The humidification chamber defines a gas flow path between a gas inlet and a gas outlet. The gas inlet is configured for fluid communication with the pressure generator outlet port. The humidifier comprises a cover configured to be moved between open and closed positions to, correspondingly allow and prevent access to an interior of the humidification chamber (e.g., to allow a user to fill and/or clean the humidification chamber). The decoupler is configured to, responsive to the cover being opened, decouple the humidification chamber gas inlet from fluid communication with the pressure generator outlet port to prevent the liquid in the humidification chamber from entering the pressure generator through the humidification chamber gas inlet and the pressure generator outlet port.

Another aspect of the present disclosure relates to a method for preventing damage from liquid spills in a humidified pressure support therapy device with a prevention system. The prevention system comprises a pressure generator, a humidifier, and a decoupler. The humidifier comprises a humidification chamber and a cover. The method comprises generating, with the pressure generator, a pressurized flow of breathable gas for delivery to an airway of a subject. The pressure generator comprises an outlet port configured to conduct the pressurized flow of breathable gas from the pressure generator. The method comprises humidifying, with the humidifier, the pressurized flow of breathable gas. The humidification comprises holding, with the humidification chamber, a liquid that humidifies the pressurized flow of breathable gas, the humidification chamber defining a gas flow path between a gas inlet and a gas outlet, the gas inlet being configured for fluid communication with the pressure generator outlet port; and covering, with the cover, the humidification chamber, the cover configured to be moved between open and closed positions to, correspondingly allow and prevent access to an interior of the humidification chamber. The method comprises decoupling, responsive to the cover being opened, the humidification chamber gas inlet from fluid communication with the pressure generator outlet port, with the decoupler, to prevent the liquid in the humidification chamber from entering the pressure generator through the humidification chamber gas inlet and the pressure generator outlet port.

Still another aspect of the present disclosure relates to a system configured to prevent damage from liquid spills in a humidified pressure support therapy device. The system comprises means for generating a pressurized flow of breathable gas for delivery to an airway of a subject, the means for generating comprising an outlet port configured to conduct the pressurized flow of breathable gas from the means for generating; means for humidifying the pressurized flow of breathable gas, the means for humidifying comprising: means for holding a liquid that humidifies the pressurized flow of breathable gas, the means for holding defining a gas flow path between a gas inlet and a gas outlet, the gas inlet being configured for fluid communication with the outlet port of the means for generating; and means for covering the means for holding configured to be moved between open and closed positions to, correspondingly allow and prevent access to an interior of the means for holding; and means for decoupling configured to, responsive to the means for covering being opened, decouple the gas inlet of the means for holding from fluid communication with the outlet port of the means for generating to prevent the liquid in the means for holding from entering the means for generating through the gas inlet and the outlet port.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
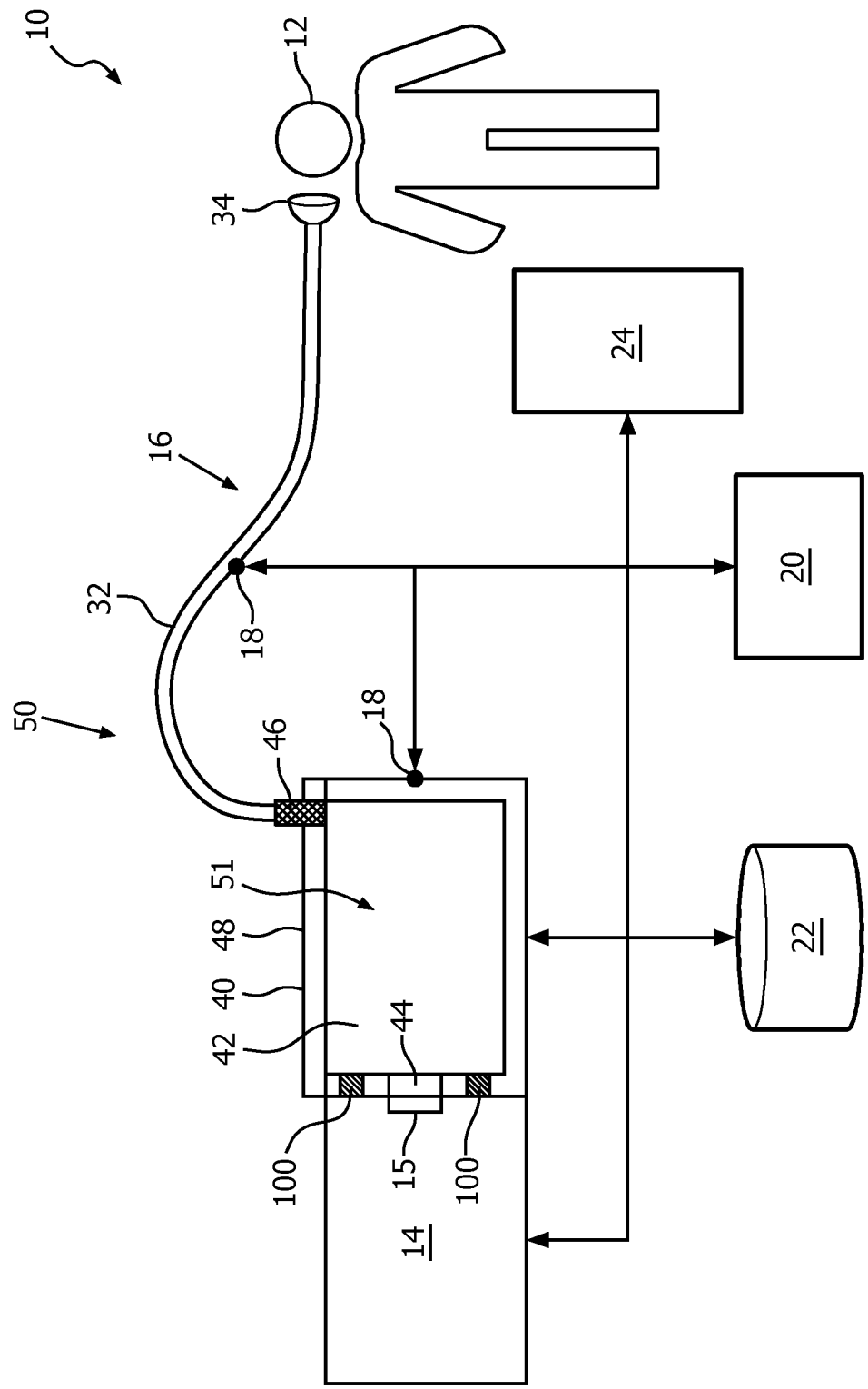
FIG. 1 illustrates a system configured to prevent damage from liquid spills in a humidified pressure support therapy device.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 illustrates a system 10 configured to prevent damage from liquid spills in a humidified pressure support therapy device 50. System 10 is configured to decouple a humidification chamber 42 in a humidifier 40 from a pressure generator 14 of pressure support therapy device 50 when a cover 48 of humidifier 40 is opened. This eliminates and/or reduces the possibility of liquid in an overfilled humidification chamber 42 unintentionally and/or otherwise entering pressure generator 14 and damaging sensitive mechanical and/or electrical components. System 10 is configured such that the decoupling is responsive to a user (e.g., a subject 12 of the therapy, a doctor, a caregiver, and/or other users) opening humidifier 40 to access humidification chamber 42 (e.g., for filling) and requires no additional action on the part of the user. In some embodiments, system 10 includes one or more of pressure generator 14, humidifier 40, subject interface 16, a sensor 18, a decoupler 100, a processor 20, electronic storage 22, a user interface 24, and/or other components.

Pressure generator 14 is configured to generate a pressurized flow of breathable gas for delivery to an airway of subject 12. In some embodiments, pressure generator 14 receives a flow of gas from a gas source, such as the ambient atmosphere, and elevates the pressure of that gas for delivery to the airway of subject 12. Pressure generator 14 is any device, such as, for example, a pump, blower, piston, or bellows, that is capable of elevating the pressure of the received gas for delivery to subject 12. The present disclosure also contemplates that gas other than ambient atmospheric air may be introduced into subject interface 15 for delivery to the patient. In such embodiments, a pressurized canister or tank of gas containing air, oxygen, and/or another gas may supply the intake of pressure generator 14. In some embodiments, pressure generator 14 is a blower that is driven at a substantially constant speed during the course of the pressure support therapy to provide the gas in subject interface 16 with a substantially constant elevated pressure and/or flow rate. Pressure generator 14 may comprise one or more valves and/or other mechanical components for controlling the pressure/flow of gas. The present disclosure also contemplates controlling the operating speed of the blower, either alone or in combination with such valves, to control the pressure/flow of gas provided to subject 12. Pressure generator 14 includes an outlet port 15 configured to conduct the pressurized flow of breathable gas from pressure generator 14 (e.g., to humidifier 40).

In some embodiments, pressure generator 14 includes electrical components (e.g., circuit boards, wiring, processors, a pressure generator user interface, indicator lights, sensor components, etc.) that facilitate control of pressure generator 14. The electrical components and/or the mechanical components (e.g., the blower, valves, etc.) of pressure generator 14 may be sensitive to moisture such that unintentional contact with a potentially damaging amount of moisture may cause pressure generator 14 to malfunction and/or not perform as described herein.

Humidifier 40 is configured to humidify the pressurized flow of breathable gas. Humidifier 40 comprises a humidification chamber 42, a heater, a cover 48, and/or other components. Humidification chamber 42 is configured to hold a liquid (e.g., water) that humidifies the pressurized flow of breathable gas. Humidification chamber 42 defines a gas flow path between a gas inlet 44 and a gas outlet 46. The gas inlet is configured for fluid communication with pressure generator outlet port 15. The gas outlet is configured for fluid communication with subject interface 16 (e.g., conduit 32). Cover 48 is configured to open and close to allow access to an interior 51 of humidification chamber 42 so that a user (e.g., subject 12, a doctor, a caregiver, and/or other users) may refill humidification chamber 42 with liquid, for example. The user may refill humidification chamber 42 while humidification chamber 42 remains in humidifier 40. In some embodiments, humidification chamber 42 may be removable from humidifier 40 when cover 48 is open. In some embodiments, cover 48 forms gas outlet 46 and/or a portion of gas outlet 46.

In some embodiments, humidifier 40 is a warm mist humidifier (e.g., a vaporizer) configured to generate water vapor by heating liquid held within humidification chamber 42 via the heater. Humidifier 40 may comprise an inductive heater configured to heat the liquid held within humidification chamber 42 via inductive heating. Humidifier 40 is configured such that the flow of gas is received from pressure generator 14 by humidifier 40 through gas inlet 44 and is humidified within humidification chamber 42 by the water vapor before being released from humidifier 40 through gas outlet 46. Gas outlet 46 is coupled with subject interface 16 such that the humidified flow of gas is delivered to the airway of subject 12 through subject interface 16.

Subject interface 16 is configured to communicate the pressurized flow of gas generated by pressure generator 14 and/or humidified by humidifier 40 to the airway of subject 12. As such, subject interface 16 comprises one or more conduits 32, an interface appliance 34, and/or other components. Conduit 32 is configured to form a flow path through which the pressurized flow of breathable gas is communicated between pressure generator 14 and/or humidifier 40 and interface appliance 34. Conduit 32 may be a flexible length of hose, and/or other conduits, that place interface appliance 34 in fluid communication with pressure generator 14 and/or humidifier 40. Interface appliance 34 is configured to deliver the flow of gas to the airway of subject 12. In some embodiments, interface appliance 34 is non-invasive. As such, interface appliance 34 non-invasively engages subject 12. Non-invasive engagement comprises removably engaging an area (or areas) surrounding one or more external orifices of the airway of subject 12 (e.g., nostrils and/or mouth) to communicate gas between the airway of subject 12 and interface appliance 34. Some examples of non-invasive interface appliance 34 may comprise, for example, a nasal cannula, a nasal mask, a nasal/oral mask, a full face mask, a total face mask, or other interface appliances that communicate a flow of gas with an airway of subject 12. The present disclosure is not limited to these examples, and contemplates delivery of the flow of gas to subject 12 using any interface appliance.

Although subject interface 16 is illustrated in FIG. 1 as a single-limbed circuit for the delivery of the flow of gas to the airway of subject 12, this is not intended to be limiting. The scope of this disclosure comprises double-limbed circuits having a first limb configured to both provide the flow of gas to the airway of subject 12, and a second limb configured to selectively exhaust gas from subject interface 16 (e.g., to exhaust exhaled gases).

Sensors 18 are configured to generate output signals conveying information related to one or more gas parameters of the gas within system 10. The gas parameters include one or more of a flow rate, a volume, a pressure, a temperature, humidity, a velocity, and/or other gas parameters. Sensors 18 may comprise one or more sensors that measure such parameters directly (e.g., through fluid communication with the flow of gas in subject interface 16). Sensors 18 may comprise one or more sensors that generate output signals related to one or more parameters of the flow of gas indirectly. For example, one or more of sensors 18 may generate an output based on an operating parameter of pressure generator 14 (e.g., a valve driver or motor current, voltage, rotational velocity, and/or other operating parameters), and/or other sensors. In some embodiments, sensors 18 may be and/or include one or more humidifier sensors 18 configured to generate output signals that convey information related to a level and/or amount of liquid in humidification chamber 42, a temperature of the liquid in humidification chamber 42, a temperature of the heater in humidifier 40, a temperature of the gas in humidification chamber 42, a humidity level, information indicating whether cover 48 is open or closed, and/or other information. The illustrated locations of sensors 18 in FIG. 1 are not intended to be limiting. Sensors 18 may comprise sensors disposed in a plurality of locations, such as for example, within pressure generator 14, within humidifier 40, within (or in communication with) conduits 32, within (or in communication with) interface appliance 34, and/or other locations. Output signals generated by sensors 18 may be transmitted wirelessly and/or via wires.

Decoupler 100 is configured to decouple humidification chamber 42 gas inlet 44 from fluid communication with pressure generator 14 outlet port 15 to prevent the liquid in humidification chamber 42 from entering pressure generator 14 through humidification chamber gas inlet 44 and pressure generator outlet port 15. Decoupler 100 is configured to decouple humidification chamber gas inlet 44 and pressure generator outlet port 15 responsive to cover 48 of humidifier 40 being opened. In some embodiments, decoupler 100 is configured to decouple humidification chamber gas inlet 44 and pressure generator outlet port 15 by causing humidification chamber 42 to physically move away from pressure generator 14. In some embodiments, decoupler 100 is configured to decouple humidification chamber gas inlet 44 and pressure generator outlet port 15 to prevent the liquid in humidification chamber 42 from entering pressure generator 14 responsive to overfill of humidification chamber 42 by a user.

Figure 2:
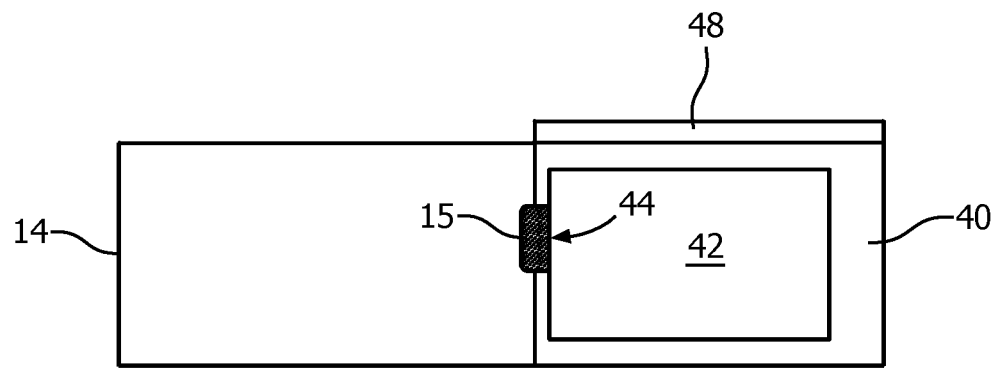
FIG. 2 illustrates a pressure generator and a humidifier.

By way of a non-limiting example, FIG. 2 illustrates pressure generator 14 and humidifier 40 (including humidification chamber 42 and cover 48). As shown in FIG. 2, cover 48 is closed and humidification chamber 42 gas inlet 44 is in fluid communication with pressure generator 14 outlet port 15.

Figure 3:
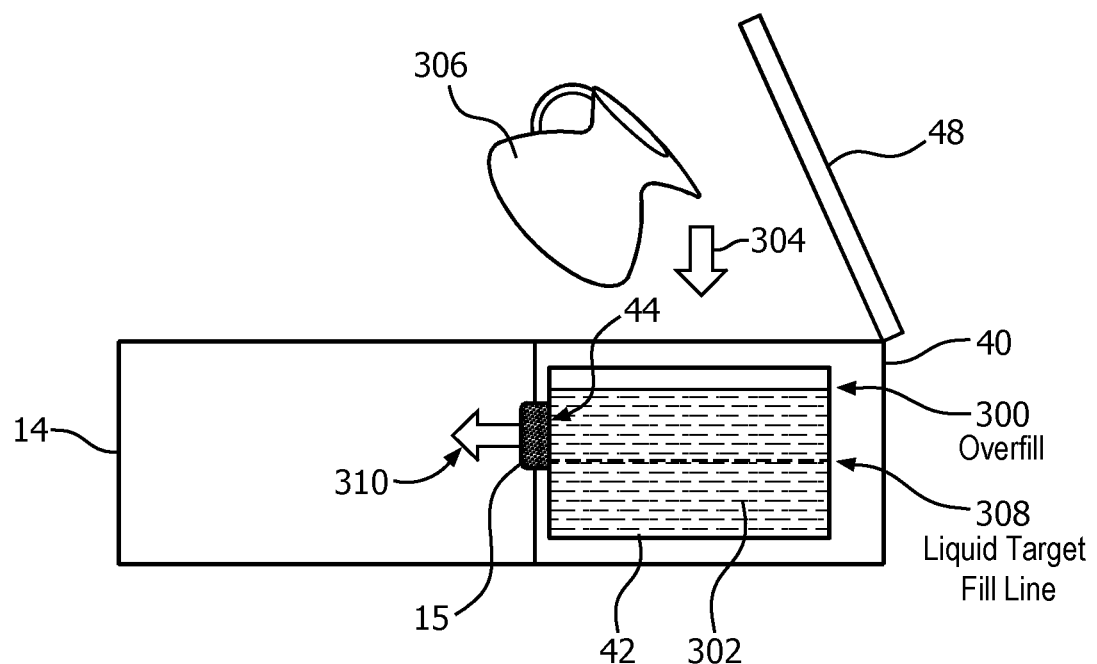
FIG. 3 illustrates an overfill use case in which liquid has been poured into a humidification chamber and the pressure generator and the humidifier chamber have not been decoupled.

FIG. 3 illustrates an overfill 300 use case in which liquid (e.g., water) 302 has been poured 304 from a pitcher (and/or any other liquid holding device) 306 into humidification chamber 42. The device shown in FIG. 3 does not include decoupler 100 (FIG. 1). Liquid 302 has filled humidification chamber 42 past a liquid target fill line 308. Filling humidification chamber 42 with liquid 302 past liquid target fill line 308 causes liquid 302 to enter 310 pressure generator 14 through humidification chamber 42 gas inlet 44 and pressure generator 14 outlet port 15 if inlet 44 and port 15 have not been decoupled. Liquid 302 that enters pressure generator 14 may damage mechanical and/or electrical components of pressure generator 14.

Figure 4:
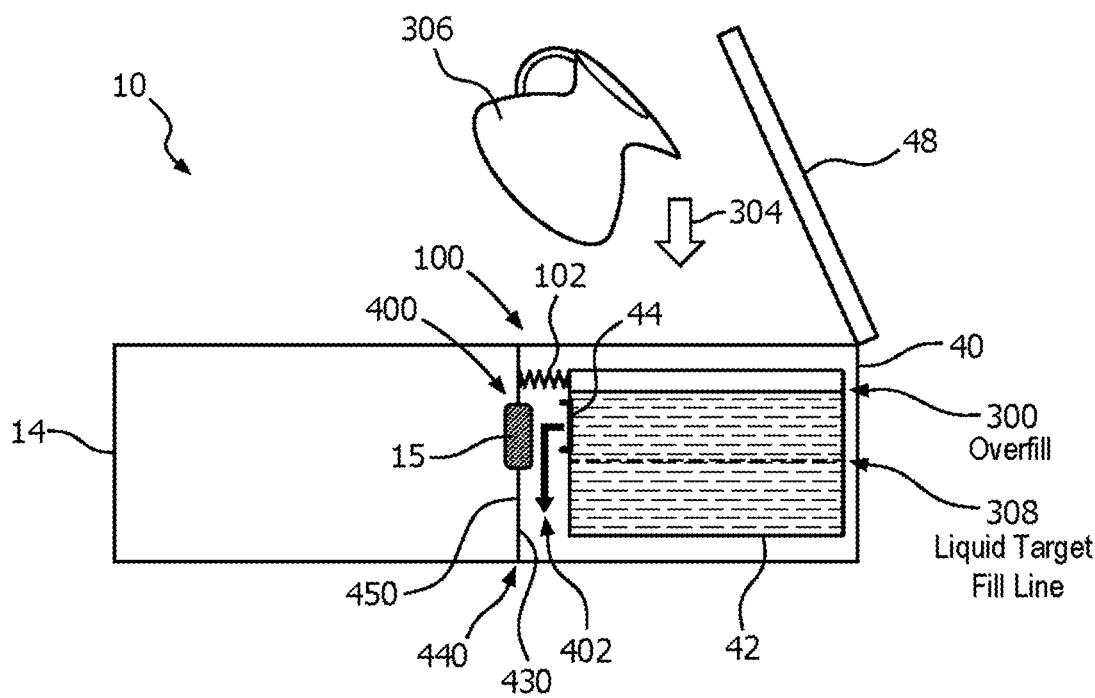
FIG. 4 illustrates an overfill use cases in which a decoupler has decoupled a humidification chamber gas inlet from fluid communication with a pressure generator outlet port.
Figure 5:
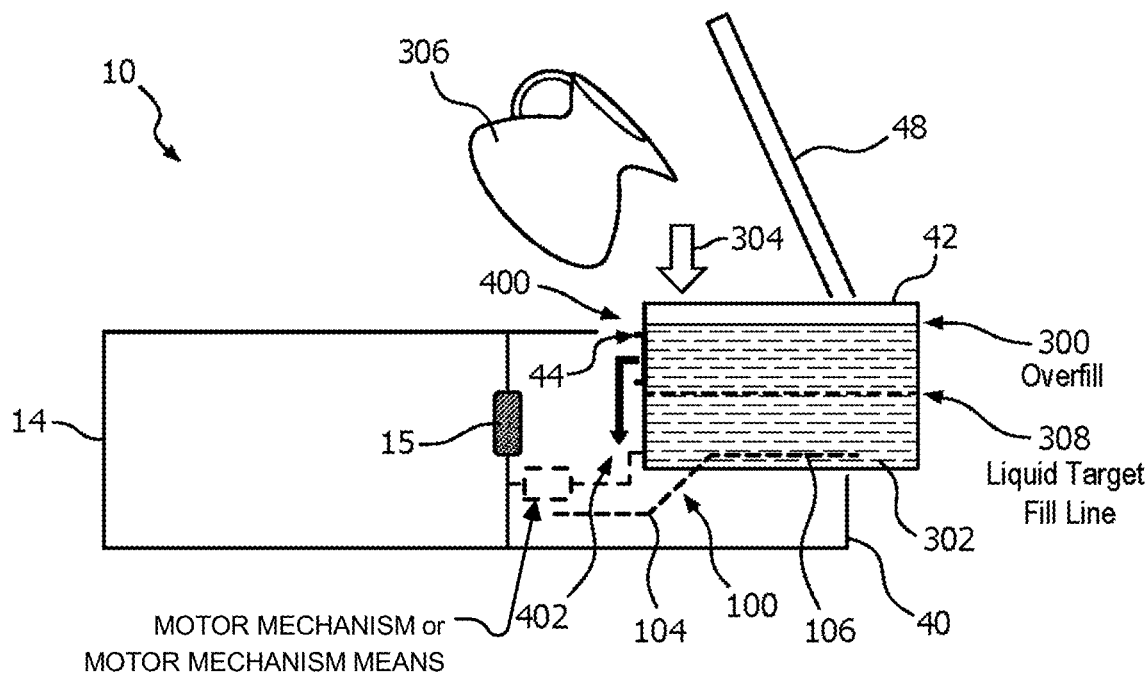
FIG. 5 illustrates an overfill use cases in which a decoupler has decoupled a humidification chamber gas inlet from fluid communication with a pressure generator outlet port.
Figure 6:
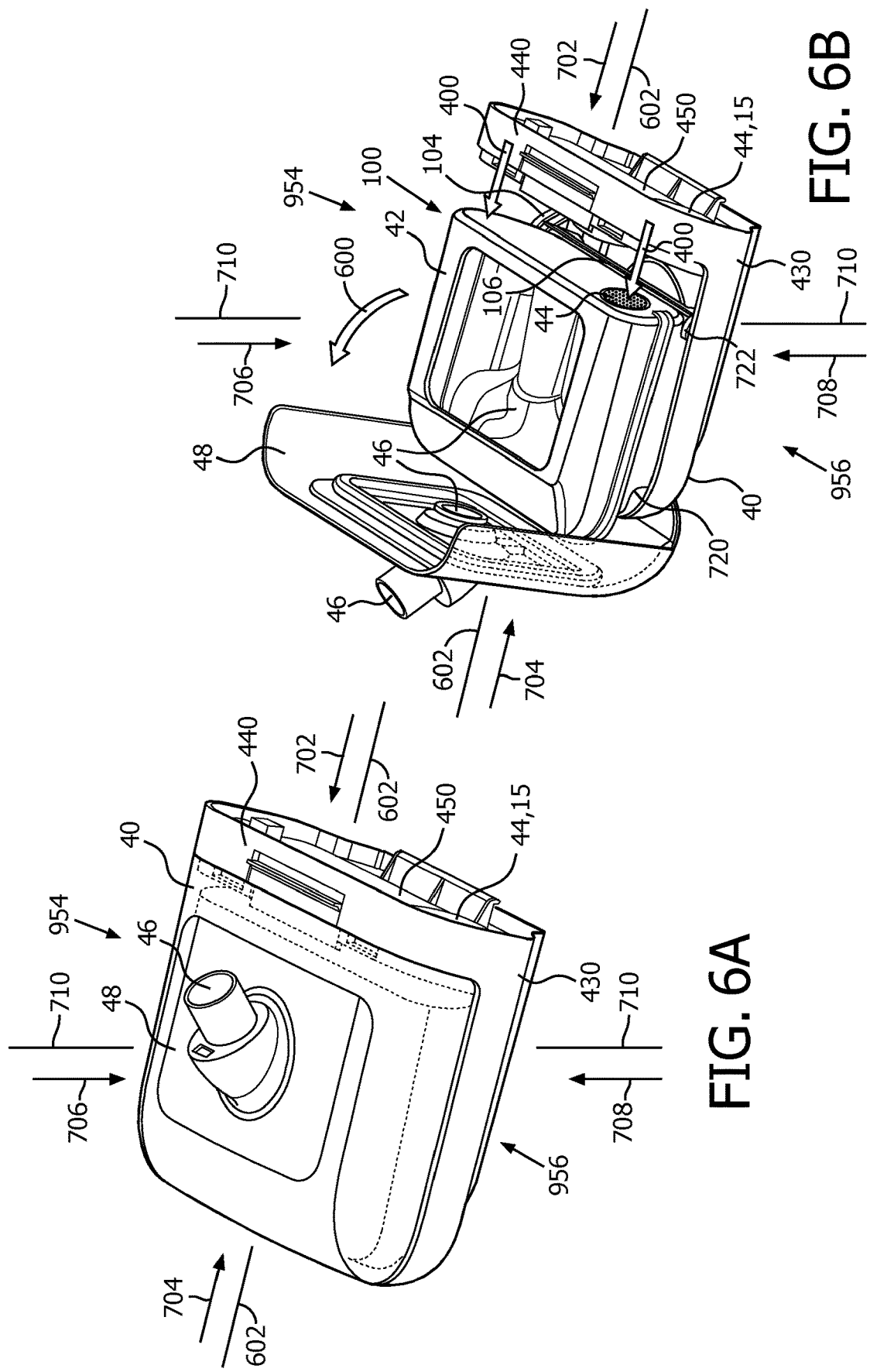
FIG. 6A illustrates a perspective view of the humidifier.
FIG. 6B illustrates a perspective view of the humidifier with a cover in an opened position.

FIGS. 4 and 5 illustrate overfill 300 use cases in which decoupler 100 has decoupled 400 humidification chamber 42 gas inlet 44 from fluid communication with pressure generator 14 outlet port 15. Liquid 302 has filled humidification chamber 42 past liquid target fill line 308 but filling humidification chamber 42 with liquid 302 past liquid target fill line 308 does not cause liquid 302 to enter 310 pressure generator 14 through humidification chamber 42 gas inlet 44 and pressure generator 14 outlet port 15. Instead, liquid 302 drains 402 through gas inlet 44 away from pressure generator 14.

As shown in FIG. 4, in some embodiments, decoupler 100 is and/or includes one or more springs and/or spring mechanisms 102 configured to push and/or otherwise move humidification chamber 42 away from pressure generator 14 (thus decoupling humidification chamber 42 gas inlet 44 from fluid communication with pressure generator 14 outlet port 15) responsive to cover 48 being opened. In some embodiments, springs and/or spring mechanisms 100 include one or more of a compression spring, a torsion spring, a coil spring, a flat spring, a machined spring, a cantilever spring, a helical spring, a leaf spring, a mainspring, magnets (e.g., magnetic forces may be used to create a force that decouples humidification chamber 42 and pressure generator 14), and/or other springs and/or spring mechanisms. Springs and/or spring mechanisms 102 may be formed from a variety of materials including metal materials, plastic materials, and/or other materials.

In some embodiments, springs and/or spring mechanisms 102 are formed as separate components within system 10. For example, springs 102 may be separately inserted into humidifier 40 between humidification chamber 42 and an outer housing 430 of humidifier 40. Humidifier 40 may be configured such that closing cover 48 causes humidification chamber 42 to compress springs 102 against outer housing 430 such that gas inlet 44 is in fluid communication with outlet port 15 of pressure generator 14. Keeping cover 48 in the closed position holds humidification chamber 42 in a position that facilitates communication with pressure generator 14 with springs 102 compressed. Opening cover 48 allows humidification chamber to be moved by springs 102 such that fluid communication between gas inlet 44 and port 15 ceases.

In some embodiments, springs and/or spring mechanisms 102 are integrated into humidifier 40. For example, outer housing 430 of humidifier 40 at a location 440 between humidification chamber 42 and pressure generator 14 may form a spring mechanism. This may include a wall 450 and/or portion of the wall 450 of outer housing 430 being formed in specific geometric shapes that bend and/or flex such that the wall 450 and/or portion of the wall 450 itself functions as a spring 102.

As shown in FIG. 5, in some embodiments, decoupler 100 comprises a track 104 and a lifting tray 106 that facilitate movement of humidification chamber 42 away from pressure generator 14 (thus decoupling humidification chamber 42 gas inlet 44 from fluid communication with pressure generator 14 outlet port 15) responsive to cover 48 being opened. In some embodiments, track 104 and lifting tray 106 are configured to raise humidification chamber 42 to enable a user to more easily remove humidification chamber 42 from humidifier 40. Track 104 and lifting tray 106 are further described below relative to FIG. 6-FIG. 9.

FIG. 6A illustrates a perspective view of humidifier 40. FIG. 6A illustrates humidifier 40 with cover 48 in a closed position. FIG. 6A illustrates gas inlet 44 and gas outlet 46, humidifier outer housing 430, and wall 450 at a location 440 between humidification chamber 42 (not shown in FIG. 6A) and pressure generator 14 (not shown in FIG. 6A). With cover 48 in a closed position, gas inlet 44 of humidification chamber 42 (not shown in FIG. 6A) is in fluid communication with pressure generator 14 outlet port 15.

FIG. 6B illustrates a perspective view of humidifier 40 with cover 48 in an opened 600 position. As shown in FIG. 6B, responsive to cover 48 being opened 600, decoupler 100 has decoupled 400 humidification chamber 42 gas inlet 44 from fluid communication with pressure generator 14 (not shown in FIG. 6B) outlet port 15. In FIG. 6B, decoupler 100 includes track 104 and lifting tray 106. In FIG. 6B, decoupler 100 causes humidification chamber 42 to move away from wall 450 (e.g., away from pressure generator 14) along a first axis 602 of humidifier 40.

Figure 7:
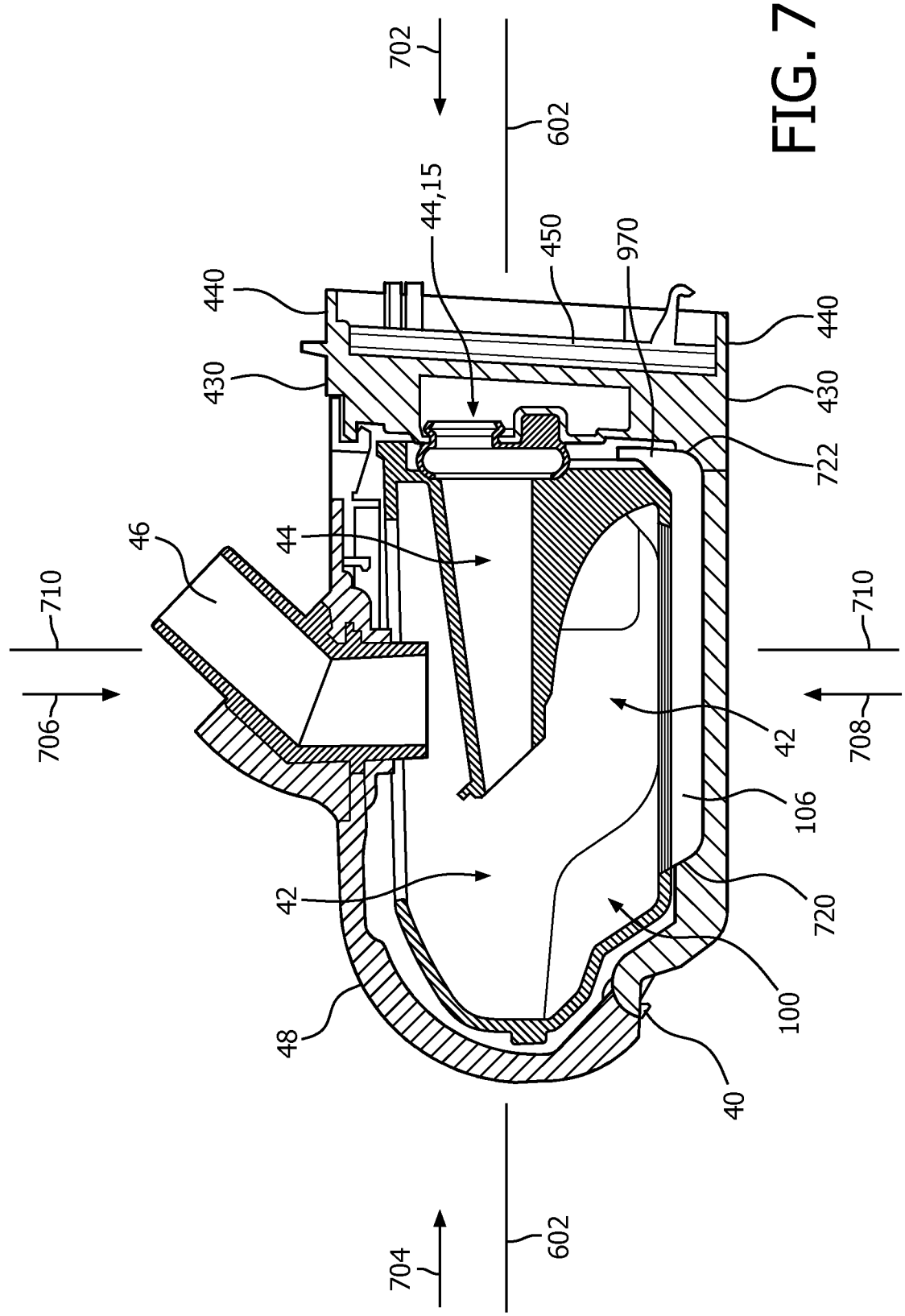
FIG. 7 illustrates a cross-sectional side view of the humidifier with the cover in a closed position.

FIG. 7 illustrates a cross-sectional side view of humidifier 40 with cover 48 in a closed position. With cover 48 in a closed position, gas inlet 44 of humidification chamber 42 is in fluid communication with pressure generator 14 (not shown in FIG. 7) outlet port 15. As shown in FIG. 7, gas inlet 44 and outlet port 15 are in fluid communication near a first side 702 of humidifier 40. Gas inlet 44 and outlet port 15 facilitate fluid communication through wall 450 at first side 702. Humidification chamber 42 is located toward a second side 704 of humidifier 40 along first axis 602. Cover 48 and gas outlet 46 are located on a third side 706 of humidifier 40. Lifting tray 106 is near a fourth side 708 of humidifier 40. Lifting tray 106 extends along first axis 602 from a position 720 near second side 704 to a position 722 near first side 702. Humidification chamber 42 is located between cover 48 and lifting tray 106 along second axis 710.

Figure 8:
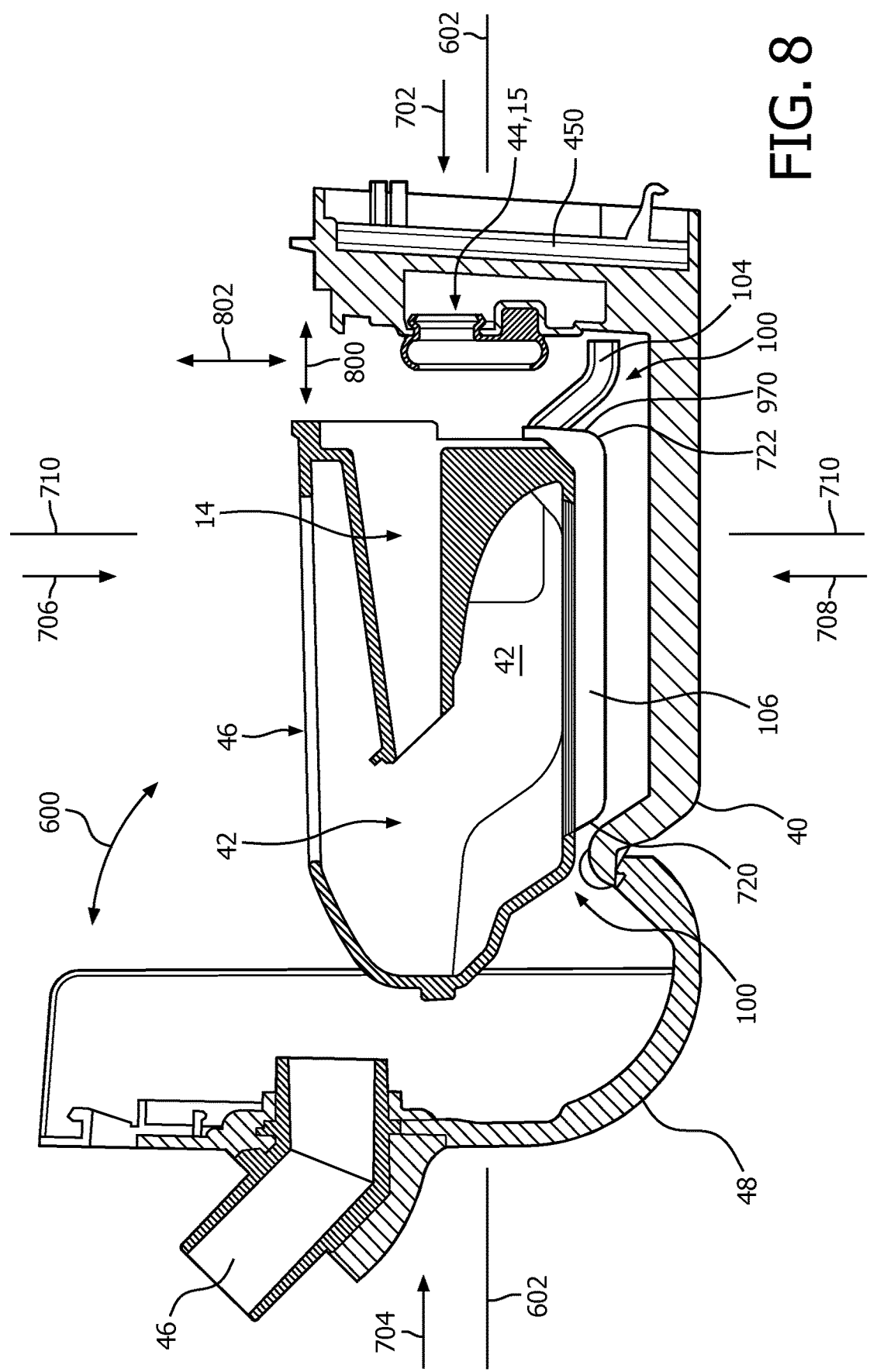
FIG. 8 illustrates a cross-sectional side view of the humidifier with the cover in an opened position.
Figure 9:
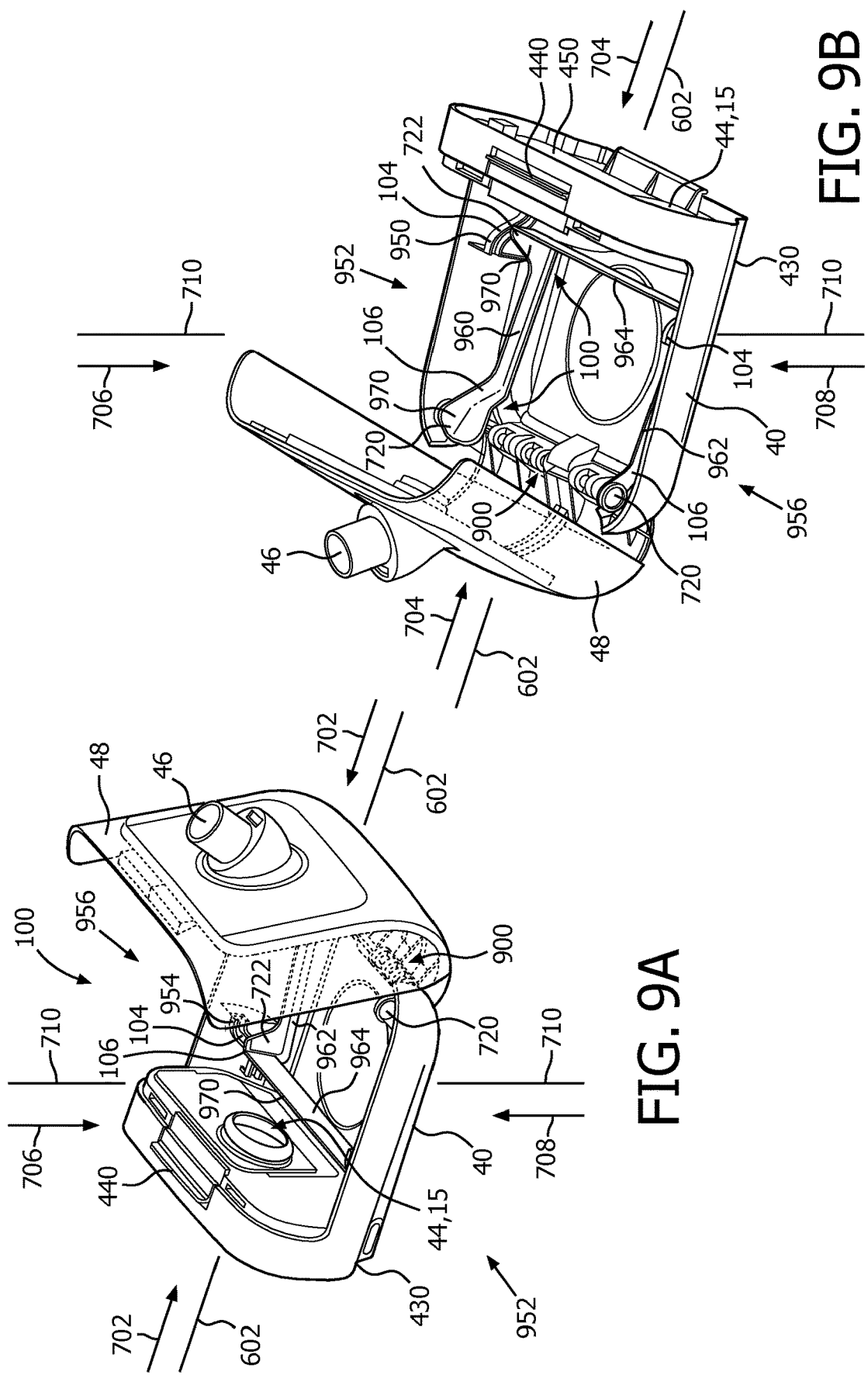
FIG. 9A illustrates the humidifier without the humidification chamber so that a track and a lifting tray are easily visible.
FIG. 9B illustrates the humidifier without the humidification chamber so that a track and a lifting tray are easily visible.

FIG. 8 illustrates a cross-sectional side view of humidifier 40 with cover 48 in an opened 600 position. In FIG. 8, humidification chamber 42 has moved 800, 802 toward second side 704 and third side 706, away from wall 450 (and pressure generator 14 not shown in FIG. 8). With cover 48 in an opened 600 position, gas inlet 44 of humidification chamber 42 is no longer in fluid communication with pressure generator outlet port 15. As shown in FIG. 7, lifting tray 106 is coupled to cover 48 at location 720 near second side 704 and fourth side 708 of humidifier 40. Lifting tray 106 extends along first axis 602 from position 720 to position 722 near first side 702 and fourth side 708 where lifting tray 106 is coupled with track 104. Lifting tray 106 supports humidification chamber 42 along first axis 602 near fourth side 708. Opening 600 cover 48 (e.g., rotation of a hinge mechanism (e.g., mechanism 900 shown in FIG. 9B below) at location 720) causes lifting tray 106 to move within track 104 toward second side 704 and third side 706 of humidifier 40. This in turn moves 800, 802 humidification chamber 42 and causes separation of gas inlet 44 from port 15.

FIG. 9A and FIG. 9B illustrate humidifier 40 without humidification chamber 42 so that track 104 and lifting tray 106 are easily visible. Track 104 and lifting tray 106 form decoupler 100. As described above, lifting tray 106 is coupled to cover 48 at location 720 near second side 704 and fourth side 708 of humidifier 40. Lifting tray 106 extends along first axis 602 from position 720 to position 722 near first side 702 and fourth side 708, where lifting tray 106 is coupled with track 104. Lifting tray 106 supports humidification chamber 42 (not shown in FIGS. 9A and 9B) along first axis 602 near fourth side 708. Opening 600 cover 48 (e.g., rotation of a hinge mechanism 900 at location 720) causes lifting tray 106 to move within track 104 toward second side 704 and third side 706 of humidifier 40. This moves humidification chamber 42 (not shown) and causes decoupling of gas inlet 44 from port 15.

As shown in FIG. 9A and FIG. 9B, track 104 is formed in and/or by outer housing 430 of humidifier 40. Track 104 may be formed in and/or by outer housing 430 via molding and/or other forming methods (e.g., at manufacture), and/or by other methods. A first portion 950 of track 104 is formed in and/or by a fifth side 952 of humidifier 40 and a second portion 954 of track 104 is formed in and/or by a sixth side 956 of humidifier 40. First portion 950 of track 104 extends from first side 702 toward second side 704 and third side 706 along fifth side 952. Second portion 954 of track 104 extends from first side 702 toward second side 704 and third side 706 along sixth side 956. First portion 950 and second portion 952 may be formed in a curved shape and/or any other shape that allows track 104 to function as described herein. In some embodiments, first portion 950 and second portion 954 are separate components that are coupled with outer housing 430 (e.g., via screws, adhesive, and/or other coupling devices).

As shown in FIGS. 9A and 9B, tray 106 may be generally "U" shaped and comprised of two members 960, 962 that are coupled with cover 48 at location 720 and extend along fifth side 952 and sixth side 956, and a third member 964 that extends from member 960 to member 962 along first side 702. Members 960, 962, and 964 may form one continuous piece and/or may be separate individual pieces that are coupled together. In some embodiments, one or more of members 960, 962, and 964 may include protrusions 970 configured ensure that humidification chamber 42 (not shown) remains supported by tray 106 when cover 48 is opened (e.g., protrusions 970 hold humidification chamber 42 on tray 106 during movement so humidification chamber 42 does not slip off of tray 106). The shape and/or features of tray 106 described above are not intended to be limiting. Tray 106 may have any shape and/or any features that allow it to function as described herein.

The springs/spring mechanism 102 and/or track 104 and lifting tray 106 described above (FIG. 4-FIG. 9B) are not intended to be limiting. The present disclosure contemplates any mechanism for decoupling humidification chamber 42 gas inlet 44 from fluid communication with pressure generator 14 outlet port 15 responsive to the opening of humidifier 40 cover 48. For example, in some embodiments, decoupler 100 may be and/or include a motor mechanism, a 4-bar mechanism, a pivoting mechanism, magnetic mechanisms (e.g., both passive and/or active like a powered actuator), ball and screw mechanisms, and/or other mechanisms (not shown) configured to cause humidification chamber 42 to move away from pressure generator 14 (thus decoupling humidification chamber 42 gas inlet 44 from fluid communication with pressure generator 14 outlet port 15). Such mechanisms may be used in addition to and/or instead of springs 102 (FIG. 4) and/or track 104 and lifting tray 106 described above.

Returning to FIG. 1, processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some implementations, processor 20 may comprise a plurality of processing units. These processing units may be physically located within the same device (e.g., pressure generator 14), or processor 20 may represent processing functionality of a plurality of devices operating in coordination.

Processor 20 is configured to control pressure generator 14 and/or humidifier 40 to generate and/or humidify the flow of gas. Processor 20 is configured to control a heater of humidifier 40 to heat the liquid in humidification chamber 42. Processor 20 is configured to control pressure generator to generate the flow of gas in accordance with a positive pressure support therapy regime. Processor 20 is configured to control pressure generator 14, humidifier 40, and/or other components of system 10 based on the output signals from sensors 18, information determined by processor 20, information entered and/or selected by a user to via user interface 24, and/or other information.

In positive airway pressure support therapy the pressurized flow of gas generated by pressure generator 14 is controlled to replace and/or compliment regular breathing of subject 12. Positive airway pressure support therapy may be used to maintain an open airway in subject 12 so that oxygen and carbon dioxide may be exchanged more easily, requiring little and/or no effort from subject 12. By way of non-limiting example, processor 20 may control pressure generator 14 such that the pressure support provided to subject 12 via the flow of gas comprises continuous positive airway pressure support (CPAP), bi-level positive airway pressure support (BPAP), proportional positive airway pressure support (PPAP), and/or other types of pressure support therapy.

CPAP supplies a fixed positive pressure to maintain a continuous level of positive airway pressure in a patient. BPAP provides a first inspiratory pressure (IPAP) and a second, typically lower, expiratory pressure (EPAP) for easier exhalation during ventilation. In some therapy modes (e.g., PPAP), processor 20 may control pressure generator 14 to apply variable pressure support in which the amount of pressure delivered to the patient during inhalation and/or during exhalation is determined and delivered on a breath by breath basis. In some embodiments, processor 20 may be configured to control pressure generator 14 to temporarily drop the supplied pressure during exhalation (C-Flex) to reduce exhalation effort required by subject 12.

In some embodiments, processor 20 is configured to control pressure generator 14 to deliver staged pressure support. In staged pressure support therapy, the pressure delivered by pressure generator 14 gradually increases over time. In some embodiments, processor 20 may control pressure generator 14 to switch therapy modes based on information related to the respiration of subject 12 and/or other information. For example, processor 20 may control pressure generator 14 to change from BPAP to CPAP after a certain number of breaths by subject 12.

In some embodiments, processor 20 is configured to control a motor mechanism of decoupler 100 to cause humidification chamber 42 to move away from pressure generator 14 responsive to information conveyed by the output signals from sensors 18 indicating that cover 48 of humidification chamber 42 has been opened. In some embodiments, sensors 18 may be and/or include a tilt sensor, an accelerometer, and/or other sensors that generate output signals that convey information indicating whether pressure generator 14 and/or humidification chamber 42 are out of a normal operating position (e.g., tilted, out of alignment, etc.). Processor 20 may be configured to control such a motor mechanism to cause humidification chamber 42 to move away from pressure generator 14 responsive to output signals conveying such information.

Electronic storage 22 comprises electronic storage media that electronically stores information. The electronic storage media of electronic storage 22 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may comprise one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 22 may store software algorithms, information determined by processor 20, information received via user interface 24, and/or other information that enables system 10 to function properly. Electronic storage 22 may be (in whole or in part) a separate component within system 10, or electronic storage 22 may be provided (in whole or in part) integrally with one or more other components of system 10 (e.g., user interface 24, pressure generator 14, processor 20, etc.).

User interface 24 is configured to provide an interface between system 10 and subject 12 and/or other users through which subject 12 and/or other users may provide information to and receive information from system 10. Other users may comprise a caregiver, a doctor, and/or other users, for example. This enables data, cues, results, and/or instructions and any other communicable items, collectively referred to as "information," to be communicated between a user (e.g., subject 12) and one or more of pressure generator 14, humidifier 40, processor 20, electronic storage 22, and/or other components of system 10. Examples of interface devices suitable for inclusion in user interface 24 comprise a keypad, buttons, switches, a keyboard, knobs, levers, a display screen, a touch screen, speakers, a microphone, an indicator light, an audible alarm, a printer, a tactile feedback device, and/or other interface devices. In one embodiment, user interface 24 comprises a plurality of separate interfaces. In one embodiment, user interface 24 comprises at least one interface that is provided integrally with pressure generator 14.

It is to be understood that other communication techniques, either hard-wired or wireless, are also contemplated by the present disclosure as user interface 24. For example, the present disclosure contemplates that user interface 24 may be integrated with a removable storage interface provided by electronic storage 22. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 24 comprise, but are not limited to, an RS-232 port, RF link, an IR link, modem (telephone, cable or other). In short, any technique for communicating information with system 10 is contemplated by the present disclosure as user interface 24.

Figure 10:
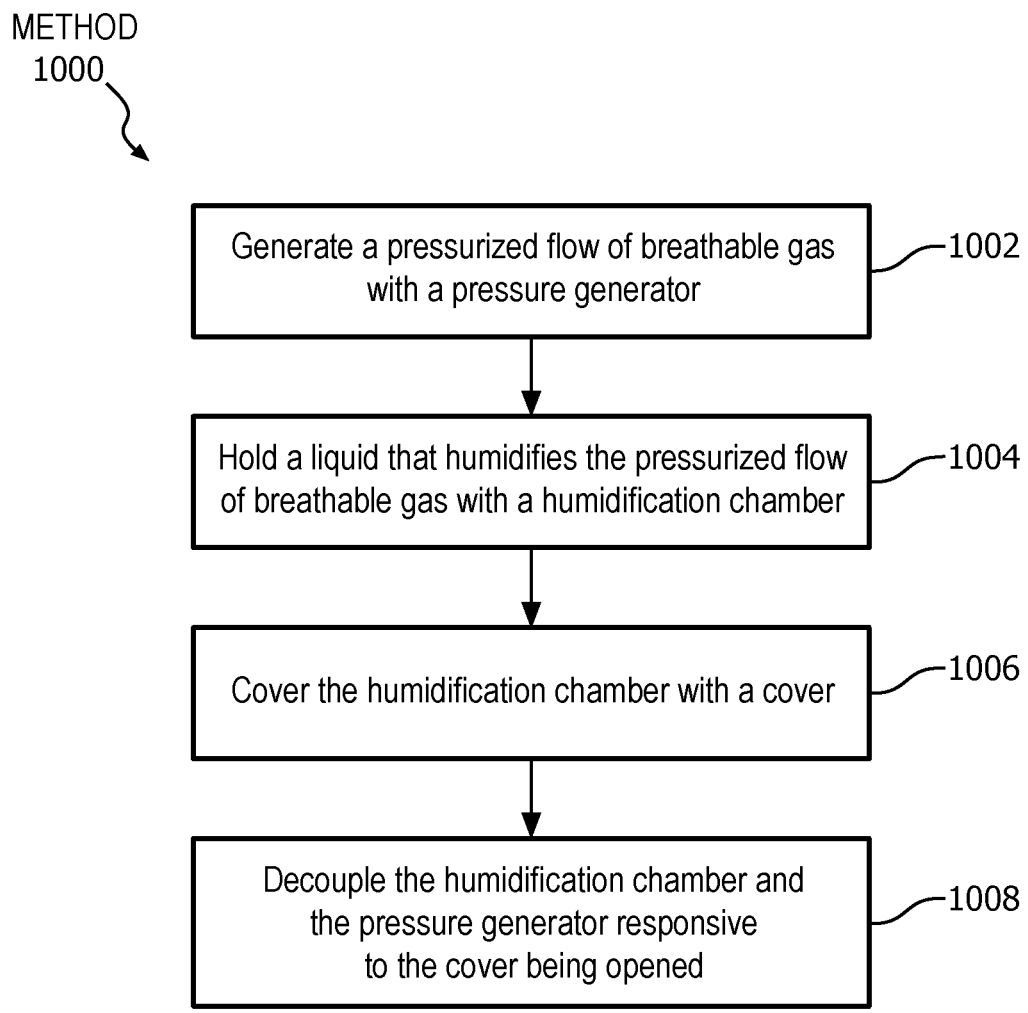
FIG. 10 illustrates a method for preventing damage from liquid spills in a humidified pressure support therapy device with a prevention system.

FIG. 10 illustrates a method 1000 for preventing damage from liquid spills in a humidified pressure support therapy device with a prevention system. The prevention system comprises a pressure generator, a humidifier, a decoupler, and/or other components. The humidifier comprises a humidification chamber and a cover. The operations of method 1000 presented below are intended to be illustrative. In some embodiments, method 1000 may be accomplished with one or more additional operations not described, and/or without one or more of the operations discussed. Additionally, the order in which the operations of method 1000 are illustrated in FIG. 10 and described below is not intended to be limiting.

In some embodiments, method 1000 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 1000 in response to instructions stored electronically on an electronic storage medium. The one or more processing devices may include one or more devices configured through hardware, firmware, and/or software to be specifically designed for execution of one or more of the operations of method 1000.

At an operation 1002, a pressurized flow of breathable gas for delivery to an airway of a subject is generated with the pressure generator. The pressure generator comprises an outlet port configured to conduct the pressurized flow of breathable gas from the pressure generator. In some embodiments, operation 1002 is performed by a pressure generator the same as or similar to pressure generator 14 (shown in FIG. 1 and described herein).

At an operation 1004, the pressurized flow of breathable gas is humidified with the humidifier. The humidifying comprises holding, with the humidification chamber, a liquid that humidifies the pressurized flow of breathable gas. The humidification chamber defines a gas flow path between a gas inlet and a gas outlet of the humidification chamber. The gas inlet is configured for fluid communication with the pressure generator outlet port. In some embodiments, operation 1004 is performed by a humidification chamber the same as or similar to humidification chamber 42 (shown in FIG. 1 and described herein).

At an operation 1006, the humidification chamber is covered with the cover. The cover is configured to be moved between open and closed to, correspondingly allow access to an interior of the humidification chamber. In some embodiments, operation 1006 includes generating, with one or more sensors of the pressure support therapy device, output signals conveying information that indicates whether the cover is open. In some embodiments, operation 1006 is performed by a cover the same as or similar to cover 48 (shown in FIG. 1 and described herein).

At an operation 1008, responsive to the cover being opened, the humidification chamber gas inlet is decoupled from fluid communication with the pressure generator outlet port with the decoupler to prevent the liquid in the humidification chamber from entering the pressure generator through the humidification chamber gas inlet and the pressure generator outlet port. In some embodiments, the decoupling is performed by one or more springs of the decoupler configured to expand and push the humidification chamber away from the pressure generator responsive to the cover being opened. In some embodiments, the decoupling is performed by a track and a lifting tray of the decoupler that facilitate movement of the humidification chamber away from the pressure generator responsive to the cover being opened. In some embodiments, the humidification chamber gas inlet and the pressure generator outlet port are decoupled to prevent the liquid in the humidification chamber from entering the pressure generator through the humidification chamber gas inlet an the pressure generator outlet port responsive to overfill of the humidification chamber by a user. In some embodiments, operation 1008 includes controlling a motor mechanism of the decoupler to cause the humidification chamber to move away from the pressure generator responsive to the information conveyed by the output signals indicating that the cover has been opened. In some embodiments, operation 1008 is performed by a decoupler the same as or similar to decoupler 100 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system configured to prevent damage from liquid spills in a humidified pressure support therapy device, the system comprising:

a pressure generator configured to generate a pressurized flow of breathable gas for delivery to an airway of a subject, the pressure generator comprising an outlet port configured to conduct the pressurized flow of breathable gas from the pressure generator;

a humidifier configured to humidify the pressurized flow of breathable gas, the humidifier comprising:

a humidification chamber configured to hold a liquid that humidifies the pressurized flow of breathable gas, the humidification chamber defining a gas flow path between a gas inlet and a gas outlet, the gas inlet being configured for fluid communication with the pressure generator outlet port; and a cover configured to be moved between open and closed positions to, correspondingly allow and prevent access to an interior of the humidification chamber; and a decoupler that comprises a track and a lifting tray, wherein the lifting tray extends along a horizontal axis of the humidifier from a front side to a back side of the humidifier for supporting the humidification chamber thereon which is located between the cover and the lifting tray along the horizontal axis at a bottom side of the humidifier, wherein the cover is coupled to the lifting tray via a hinge mechanism of the humidifier at a first end of the lifting tray, further at a first location at a front of the bottom side of the humidifier, wherein the lifting tray is further coupled to the track at a second end of the lifting tray, opposite to the first end, further at a second location at a back of the bottom side of the humidifier, the decoupler being configured to decouple the humidification chamber gas inlet from fluid communication with the pressure generator outlet port in response to the cover being moved from the closed position to the open position, which corresponds to the cover being opened, wherein opening the cover causes the lifting tray, which is supporting the humidification chamber thereon and coupled at the first end to the cover via the hinge mechanism of the humidifier at the front of the bottom side of the humidifier and coupled to the track at the second end, opposite to the first end, to move within the track from the back of the bottom side of the humidifier towards a front of a top side of the humidifier and thereby decouple the humidification chamber gas inlet from fluid communication with the pressure generator outlet port, wherein decoupling the humidification chamber gas inlet from fluid communication with the pressure generator outlet port, via the decoupler, prevents the liquid in the humidification chamber from entering the pressure generator through the humidification chamber gas inlet and the pressure generator outlet port.

2. The system of claim 1, wherein the decoupler further comprises one or more springs, coupled between an inner wall of the humidifier and the humidification chamber, configured to expand and push the humidification chamber away from the pressure generator in response to the cover being opened.

3. The system of claim 2, wherein the one or more springs are selected from the group consisting of a compression spring, a torsion spring, a coil spring, a flat spring, a machined spring, a cantilever spring, a helical spring, a leaf spring, a mainspring, and a pair of magnets, wherein the pair of magnets provide a magnetic spring force.

4. The system of claim 3, wherein the one or more springs are formed from one or more of metal materials, plastic materials, and materials other than metal and plastic materials.

5. The system of claim 1, wherein the decoupler is configured to decouple the humidification chamber gas inlet from fluid communication with the pressure generator outlet port to prevent the liquid in the humidification chamber from entering the pressure generator through the humidification chamber gas inlet and the pressure generator outlet port in response to an overfill of the liquid in the humidification chamber by a user.

6. A method for preventing damage from liquid spills in a humidified pressure support therapy device with a prevention system, wherein the prevention system comprises a pressure generator, a humidifier, and a decoupler, further wherein the humidifier comprises a humidification chamber and a cover, the method comprising:

generating, with the pressure generator, a pressurized flow of breathable gas for delivery to an airway of a subject, wherein the pressure generator includes an outlet port configured to conduct the pressurized flow of breathable gas from the pressure generator;

humidifying, via the humidifier, the pressurized flow of breathable gas, wherein the act of humidifying comprises:

holding, via the humidification chamber, a liquid that humidifies the pressurized flow of breathable gas, wherein the humidification chamber defines a gas flow path between a gas inlet of the humidification chamber and a gas outlet of the humidification chamber, the gas inlet being configured for fluid communication with the pressure generator outlet port; and covering, via the cover, the humidification chamber, wherein the cover is configured to be moved between an open position and a closed position to, correspondingly allow and prevent access to an interior of the humidification chamber; and decoupling, via a decoupler that comprises a track and a lifting tray, wherein the lifting tray extends along a horizontal axis of the humidifier from a front side to a back side of the humidifier for supporting the humidification chamber thereon which is located between the cover and the lifting tray along the horizontal axis at a bottom side of the humidifier, wherein the cover is coupled to the lifting tray via a hinge mechanism of the humidifier at a first end of the lifting tray, further at a first location at a front of the bottom side of the humidifier, wherein the lifting tray is further coupled to the track at a second end of the lifting tray, opposite to the first end, further at a second location at a back of the bottom side of the humidifier; the humidification chamber gas inlet from fluid communication with the pressure generator outlet port in response to the cover being moved from the closed position to the open position, which corresponds to the cover being opened, wherein opening the cover causes the lifting tray, which is supporting the humidification chamber thereon and coupled at the first end to the cover via the hinge mechanism of the humidifier at the front of the bottom side of the humidifier and coupled to the track at the second end, opposite to the first end, to move within the track from the back of the bottom side of the humidifier towards a front of a top side of the humidifier and thereby decouple the humidification chamber gas inlet from fluid communication with the pressure generator outlet port, wherein decoupling the humidification chamber gas inlet from fluid communication with the pressure generator outlet port, via the decoupler, prevents the liquid in the humidification chamber from entering the pressure generator through the humidification chamber gas inlet and the pressure generator outlet port.

7. The method of claim 6, wherein the decoupling is further performed by one or more springs of the decoupler, coupled between an inner wall of the humidifier and the humidification chamber, configured to expand and push the humidification chamber away from the pressure generator in response to the cover being opened.

8. The method of claim 6, further comprising decoupling the humidification chamber gas inlet from fluid communication with the pressure generator outlet port to prevent the liquid in the humidification chamber from entering the pressure generator through the humidification chamber gas inlet and the pressure generator outlet port in response to an overfill of the liquid in the humidification chamber by a user.

9. A system configured to prevent damage from liquid spills in a humidified pressure support therapy device, the system comprising:
   means for generating a pressurized flow of breathable gas for delivery to an airway of a subject, the means for generating comprising an outlet port configured to conduct the pressurized flow of breathable gas from the means for generating;
   a humidifier for humidifying the pressurized flow of breathable gas, the humidifier comprising:
      means for holding a liquid that humidifies the pressurized flow of breathable gas, the means for holding defining a gas flow path between a gas inlet and a gas outlet, the gas inlet being configured for fluid communication with the outlet port of the means for generating; and
      means for covering the means for holding configured to be moved between open and closed positions to correspondingly allow and prevent access to an interior of the means for holding; and
      means for decoupling that comprises a track and a lifting tray, wherein the lifting tray extends along a horizontal axis of the humidifier from a front side to a back side of the humidifier for supporting the means for holding thereon which is located between the cover and the lifting tray along the horizontal axis at a bottom side of the humidifier, wherein the means for covering is coupled to the lifting tray via a hinge mechanism of the humidifier at a first end of the lifting tray, further at a first location at a front of the bottom side of the humidifier, wherein the lifting tray is further coupled to the track at a second end of the lifting tray, opposite to the first end, further at a second location at a back of the bottom side of the humidifier, the means for decoupling being configured to decouple the gas inlet of the means for holding from fluid communication with the outlet port of the means for generating in response to the means for covering being moved from the closed position to the open position, which corresponds to the means for covering being opened, wherein opening the means for covering causes the lifting tray, which is supporting the humidification chamber thereon and coupled at the first end to the cover via the hinge mechanism of the humidifier at the front of the bottom side of the humidifier and coupled to the track at the second end, opposite to the first end, to move within the track from the back of the bottom side of the humidifier towards a front of a top side of the humidifier and thereby decouple the gas inlet of the means for holding from fluid communication with the outlet port of the means for generating, wherein decoupling of the gas inlet from fluid communication with the outlet port, via the means for decoupling, prevents the liquid in the means for holding from entering the means for generating through the gas inlet and the outlet port.

10. The system of claim 9, wherein the means for decoupling further comprises one or more springs, coupled between an inner wall of the humidifier and the means for holding, configured to expand and push the means for holding away from the means for generating in response to the means for covering being opened.

11. The system of claim 9, wherein the means for decoupling is configured to decouple the gas inlet of the means for holding from fluid communication with the outlet port of the means for generating to prevent the liquid in the means for holding from entering the means for generating through the gas inlet of the means for holding and the outlet port of the means for generating in response to an overfill of the liquid in the means for holding by a user.

* * * * *